US011364391B2

(12) United States Patent
Daffer

(10) Patent No.: US 11,364,391 B2
(45) Date of Patent: Jun. 21, 2022

(54) CONTROLLABLE PHOTONIC CHAMBER

(71) Applicant: Visibelle Derma Institute, Inc., Bloomington, MN (US)

(72) Inventor: Steven J. Daffer, Edina, MN (US)

(73) Assignee: VISIBELLE DERMA INSTITUTE, INC., Bloomington, MN (US)

(*) Notice: Subject to any disclaimer, the term of this patent is extended or adjusted under 35 U.S.C. 154(b) by 0 days.

(21) Appl. No.: 16/895,849

(22) Filed: Jun. 8, 2020

(65) Prior Publication Data

US 2020/0384288 A1 Dec. 10, 2020

Related U.S. Application Data

(60) Provisional application No. 62/858,058, filed on Jun. 6, 2019.

(51) Int. Cl.
*A61N 5/06* (2006.01)
*A61L 31/02* (2006.01)

(52) U.S. Cl.
CPC .......... *A61N 5/0625* (2013.01); *A61L 31/028* (2013.01); *A61N 5/0616* (2013.01); *A61N 2005/064* (2013.01); *A61N 2005/066* (2013.01); *A61N 2005/0663* (2013.01)

(58) Field of Classification Search
CPC ................................................. A61N 2005/06
See application file for complete search history.

(56) References Cited

U.S. PATENT DOCUMENTS

| 4,546,236 | A  | * | 10/1985 | Janson ................ A61H 33/063 248/201 |
| 5,255,399 | A  |   | 10/1993 | Park |
| D341,425  | S  |   | 11/1993 | Lee |
| 6,745,411 | B1 |   | 6/2004  | Kjonaas |
| 9,629,777 | B2 |   | 4/2017  | Shurtleff |
| D859,674  | S  |   | 9/2019  | Smith |
| 2006/0059618 | A1 | * | 3/2006 | Chung ............... A61H 33/6089 4/622 |
| 2007/0235439 | A1 | * | 10/2007 | Chen ..................... F24H 3/002 219/450.1 |
| 2007/0294819 | A1 |   | 12/2007 | Levesque |
| 2009/0126098 | A1 |   | 5/2009  | Gong |

(Continued)

FOREIGN PATENT DOCUMENTS

| EP | 1593914 A2 * | 11/2005 | ............ F21V 33/006 |
| KR | 100581764 B1 | 12/2005 | |

OTHER PUBLICATIONS https://www.covewellness.com/jade-infrared-saunas/ (Year: 2017).*

*Primary Examiner* — Nathan J Jenness
*Assistant Examiner* — Skylar Lindsey Christianson
(74) *Attorney, Agent, or Firm* — Peter J. Ims; Westman, Champlin & Koehler, P.A.

(57) ABSTRACT

A chamber providing controlled amounts of IR and visible light within an internal space sized to seat at least one human being. The chamber includes at least one heater configured to emit FIR energy, at least one heater configured to emit NIR energy, and at least one heater configured to emit at least MIR energy. The chamber includes at least one light emitting source configured to emit a selected wavelength of visible light, and a control panel configured to control the amount and duration of FIR, MIR, NIR and visible light within the chamber.

18 Claims, 3 Drawing Sheets

(56) References Cited

U.S. PATENT DOCUMENTS

| | | | |
|---|---|---|---|
| 2013/0042402 A1* | 2/2013 | Parker | A61H 33/066 |
| | | | 4/524 |
| 2014/0157511 A1 | 6/2014 | Shurtleff | |
| 2014/0209594 A1* | 7/2014 | Besner | A61F 7/007 |
| | | | 219/217 |
| 2015/0127076 A1* | 5/2015 | Johnson | A61N 5/06 |
| | | | 607/90 |
| 2016/0310776 A1 | 10/2016 | Smith | |
| 2017/0056718 A1 | 3/2017 | Davis | |
| 2020/0398078 A1* | 12/2020 | Jensen | H05B 3/20 |

\* cited by examiner

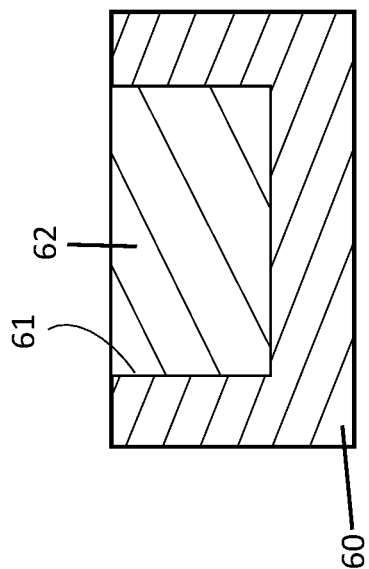
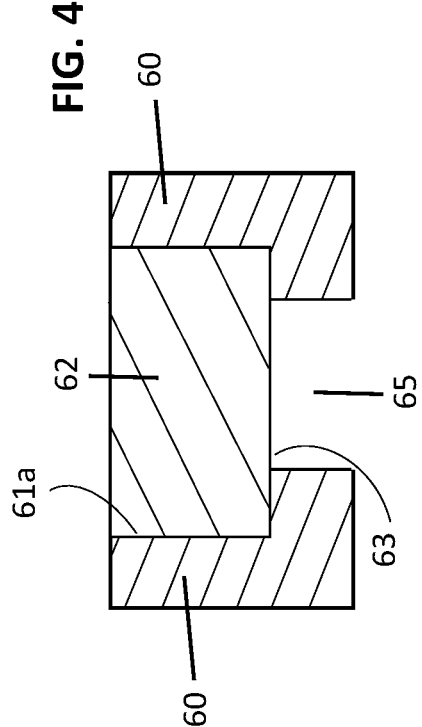
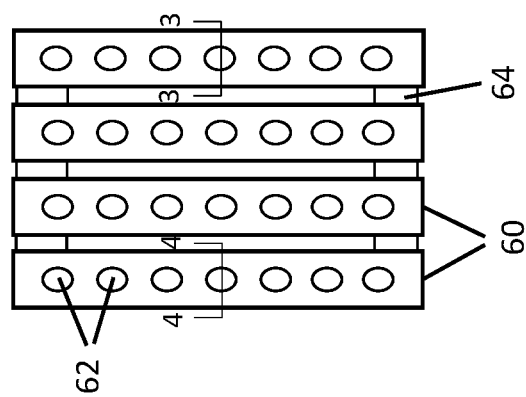

CONTROLLABLE PHOTONIC CHAMBER

CROSS-REFERENCE TO RELATED APPLICATION

This application is based on and claims the benefit of U.S. provisional application Ser. No. 62/858,058, filed Jun. 6, 2019, the content of which is hereby incorporated in its entirety.

BACKGROUND

The present disclosure relates to a chamber in which the amount and type of beneficial photonic energy delivered to a person is controlled within a chamber. In particular, the present disclosure includes a chamber that provides selected wavelengths and dosages of infrared and visible light that are beneficial to a human being while eliminating photonic energy that is damaging to at least the skin of the human being.

Many people seek the benefits of the sun for the health benefits that the visible and infrared spectrum provides to the human body. These benefits include warmth from the IR spectrum and certain wavelengths that provide healing, aesthetic enhancements and wellness to the body. However, the sun includes the complete spectrum including the ultraviolet spectrum that damages the skin and can cause adverse skin lesions and cancer, aging and wrinkles.

Many people also use saunas to provide thermal benefits to the body. However, typical saunas use heat or infrared sources that are not controllable. For instance, when heated bodies, such as hot rocks are utilized, the only way to control the temperature in the sauna is to add or remove heated bodies, which can lead to temperatures that exceed the upper limit of hyperthermic benefits to the body or are below the lower end of the range of temperatures that provide hyperthermic benefits to the body.

Some people utilize dry saunas that utilize heat generated by heaters that produce far infrared (FIR) energy. FIR energy is typically defined as radiation with a wavelength of 15,000 nm to about 100,000 nm (corresponding to a range of about 20 THz to 300 GHz). However, while heating a person's body, FIR energy does not provide a quick sensation of heating the body.

SUMMARY

An aspect of the present disclosure relates to a chamber providing controlled amounts of IR and visible light within an internal space sized for standing or seating of at least one human being. The chamber includes at least one emitter system or heater configured to emit far-infrared (FIR) energy, at least one emitter system or heater configured to emit near-infrared (NIR) energy, and at least one emitter system or heater configured to emit at least mid-infrared (MIR) energy. The chamber includes at least one light emitting source configured to emit at least one selected wavelength of visible light, and a control panel configured to control the amount and duration of FIR, MIR, NIR and visible light within the chamber.

In some aspects, the FIR, MIR, and NIR emitters are activated concurrently to generate effecting near, mid-range, and far infrared heating of the interior of the chamber. This results in a reduction of the time it takes to heat the interior of the chamber to a selected temperature while also providing benefits of each type of IR.

In some aspects, natural stones are placed within the internal space, where the natural stone emits wavelengths of infrared photons when heated. Exemplary natural stones include, but are not limited to, jade, quartz, germanium, Bian, and tourmaline. In some instances, the natural stones are placed directly in front of IR heaters, which aid in the emission of infrared wavelengths from the natural stones. In some instances, the heat within the chamber is used to heat the natural stones to cause infrared photons to be emitted. In some instances, fragrant plants, such as herbs, are heated in the internal space to emit aromas that are beneficial. Exemplary herbs for use to provide aroma therapy include, but are not limited to, eucalyptus and rosemary.

In some aspects, visible wavelength light can be utilized with the multi-spectrum IR photonic energy. For instance, by non-limiting example, red light having a 640 nm wavelength can be utilized within the chamber along with the multi-spectrum IR photonic energy.

In other aspects, the chamber can include blocks of mineral salt that when heated emit ions that cleanse the air.

BRIEF DESCRIPTION OF THE DRAWINGS

FIG. 2 is a schematic view of a grid containing natural stones.

FIG. 3 is a sectional view take along section line 3-3 in FIG. 2.

FIG. 4 is a sectional view take along section line 4-4 in FIG. 2.

DETAILED DESCRIPTION

Figure 1:
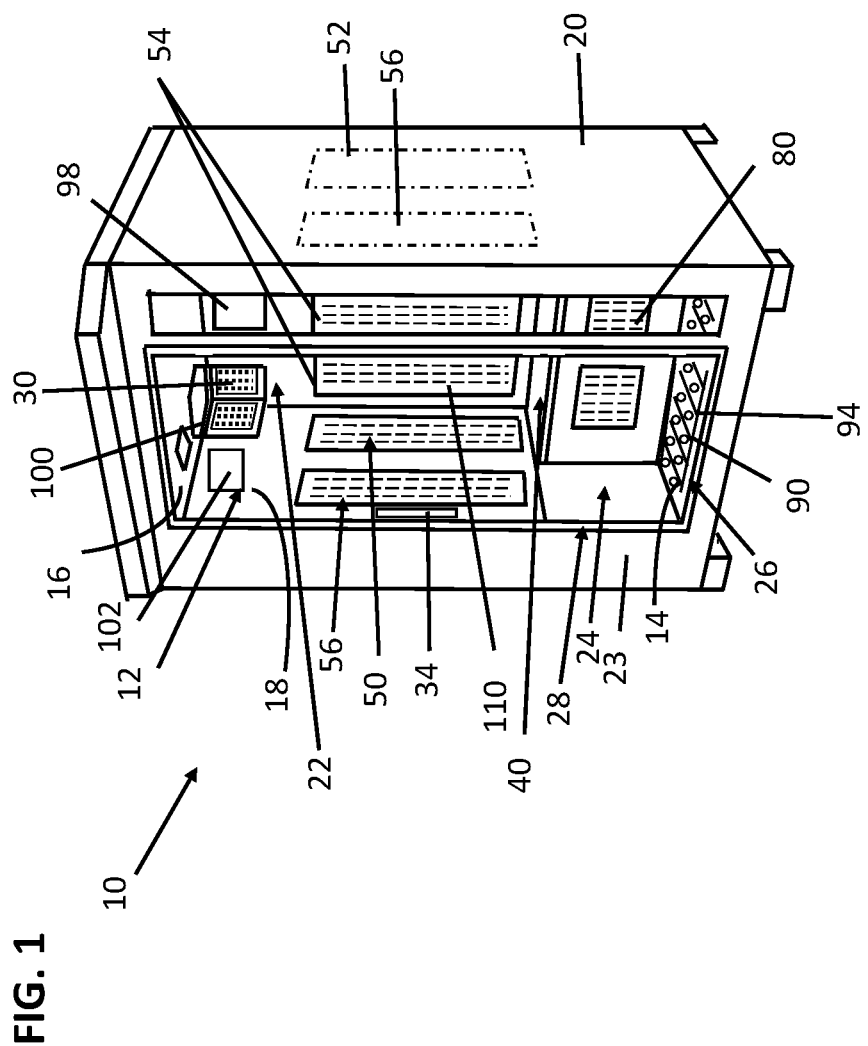
FIG. 1 is a perspective view of a controllable photonic chamber.

The present disclosure is directed to a chamber 10 having an internal space 12 that is of a sufficient size to comfortably sit one or more people. In exemplary embodiments, the internal space 12 is configured comfortably sit up to four adults. However, a chamber 10 with an internal space 12 configured to sit any number of people. The chamber 10 includes a plurality of IR heaters, panels of natural stones and panels of visible light to provide a controllable photonic environment for a person(s) that provides the beneficial IR photonic energy and the beneficial visible light photonic energy, while eliminating the photonic energy that is harmful to a person's body, such as ultraviolet light and wavelengths that are shorter than the visible and infrared spectrums.

The chamber 10 includes a floor 14 and a ceiling 16 that are connected by left and right sidewalls 18 and 20. A back wall 22 connects the left and right sidewalls 18 and 20 and the floor 14 and ceiling 16. A front wall 23 connects the left and right sidewalls 18 and 20 and the floor 14 and ceiling 16. The front wall 23 includes a window 24 such that a person can see into and out of the chamber 10. Inner surfaces of the floor 14, the ceiling 16, the left and right sidewalls 18 and 20, the back wall 22 and the front wall 23 define the internal space 12.

The front wall 23 includes an opening 26 that is configured to accept a door 28 that is hingedly attached to the front wall 23 with at least upper and lower hinges (not shown). The door 28 includes a handle 34 on an outside surface of the door 28 and an inside surface of the door 28, where the handle 34 is typically constructed of a material that does not readily conduct heat to prevent the handle from becoming hot to the touch when the internal space 12 is heated. An exemplary, but non-limiting, material for the handle 34 is wood.

The chamber 10 includes a plurality of IR heaters that output photons in the near infrared spectrum (NIR), the mid infrared spectrum (MIR) and the far infrared spectrum (FIR). The NIR has a range of wavelengths from about 700 nm to about 1,500 nm. The MIR has a range of wavelengths from about 1,500 nm to about 5,600 nm. The FIR has a range of wavelengths from about 5,600 nm to about 100,000 nm. Utilizing the plurality of IR heaters that emit photons in the NIR, MIR and FIR frequencies, the person experiences the benefits of each spectrum of frequencies. For instance, the NIR has shorter wave frequencies which heats the top layer of the skin such that the person experiences the sensation of heat almost immediately upon entering the energized photonic chamber. The MIR provides for total body heating while the FIR provides deep heating the to the person's body. Therefore, the person experiences a nearly immediate photonic experience from the NIR and over time experiences the medium and deeper photonic experiences of the MIR and FIR.

The chamber 10 includes a seat 40 that extends from the left sidewall 18 to the right sidewall 20 where the seat 40 has a length that is configured to comfortably allow two people to sit in the internal space 12 of the chamber 10. The plurality of IR heaters is strategically located about the seat 40 to provide the NIR, MIR and FIR frequencies.

The chamber 10 includes a left NIR/MIR heater 50 located on the left sidewall 18 and above the seat 40 proximate the back wall 22 and a right NIR/MIR heater located on the right sidewall 20 opposite the left NIR/MIR heater 52 and above the seat 40 proximate the back wall 22. The left and right NIR/MIR heaters 50 and 52 emit a full spectrum of NIR/MIR photons on opposing sides of a seated person such that the NIR/MIR photons provide a balance of NIR/MIR energy absorbed by the body and provide the sensation of near immediate heating upon energizing the heaters in the chamber 10 and sitting on the seat 40. By way of non-limiting example the left and right NIR/MIR heaters 50 and 52 are constructed of an iron material that emits IR in the near wavelengths and of a ceramic material that emits IR in the mid wavelengths. However, other materials of construction for the heaters 50 and 52 are within the scope of the present disclosure.

The chamber 10 includes three FIR heaters 54 located along and on the back wall 22. The three FIR heaters 54 are substantially the same size and substantially span the width of the back wall 22 above the seat 40. A typical FIR heater 54 includes carbon fiber heaters that emit FIR photons. As previously mentioned, the FIR heaters 54 emit photons that provide deeper penetration of the skin that does not provide the immediate sensation of heat. However, over time, the FIR heaters the body can feel the energy imparted into the body in the form of heat.

The chamber includes left and right FIR heaters 56 that are located on the left and right sidewalls 18 and 20, respectively. The FIR heaters 56 are substantially the same size and configuration as the heaters 54. However, as illustrated in FIG. 2, the FIR heaters 56 are covered by grids 58 that are similarly constructed to retain natural stones that, when heated, emit desired IR energy.

Referring to FIGS. 2-4, the grids 58 include a plurality of spaced apart boards 60 that include cavities 61 configured to accept the natural stones 62 where the spaced apart boards 60 are secured together with at least end boards 64. The spaces between the boards 60 allows some of the FIR photons to pass into the chamber while other photons engage the board 60

In one embodiment, the cavities 61 do not pass through the boards 60 and rely on IR heating as the chamber heats. In another embodiment, the cavities 61a pass through the boards 60, and the stones are retained by a shoulder 63. However, the opening 65 in the back side of the boards 60 proximate the FIR heaters 56 allows for FIR photons to directly contact the back side of the stones 62, resulting a more rapid heating a quicker release of the FIR photons from the stones. A typical stone 60 that is utilized is jade. However, any natural stone that emits a desired IR wavelength(s) can be utilized. Additional stones include quartz, germanium, Bian, and tourmaline, for example. As many as eighty (80) or more natural stones may be incorporated into the chamber through one or more grids 58. While the grids are typically constructed of wood boards, the grids can be constructed of any suitable material that can withstand the heat of the sauna over extended periods of time and numerous thermal cycles while being safe for humans to be around over extended periods of time.

In one embodiment, the grids 58 are secured directly to the left and right sidewalls 18 and 20, respectively. This allows the user to select and use the desired chamber 10 with the selected stones 62 in a maintenance free manner.

Figure 5:
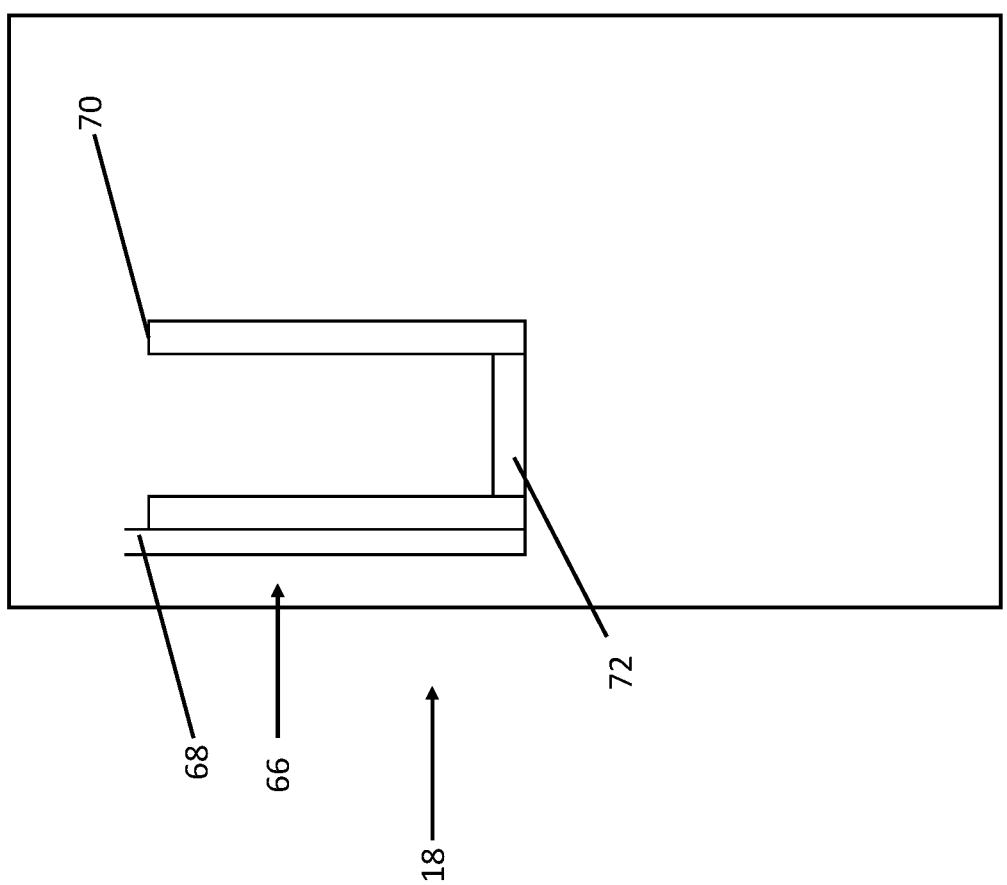
FIG. 5 is a schematic view of a wall with a bracket for removably retaining a grid having natural stones.

In another embodiment, as illustrated in FIG. 5, the sidewalls 18 and/or 20 have brackets 66 having a first channel 68, a second channel 70 and a bottom stop 72. The brackets 66 allow grids 58 containing different natural stones to be selected and used to provide a desired emitted IR frequency. Further, the chamber 10 can be provided with any number of grids 58 with different stones as desired by the user. By way of non-limiting example, the grids 58 with jade can be slidably removed from the brackets 66 and replaced with grids 58 contain quartz.

Referring back to FIG. 1, the chamber 10 includes a FIR/MIR heater 80 below the seat 40 to ensure even heating proximate the floor 14 within the chamber. The FIR/MIR heater 80 can be any suitable heater that emits FIR/MIR wavelength energy including, but not limited to, a ceramic heater.

While the NIR/MIR/FIR heaters are described being in a particular location and emitting a particular spectrum of wavelengths, the present disclosure is not limited to the specific configuration of heaters. Rather, any number of NIR/MIR/FIR heaters can be utilized provided that the substantially full spectrum of IR energy is emitted within the internal cavity 12 of the chamber 10.

The chamber 10 includes a grid 90 secured to the floor 14. The grid 90 includes spaced apart boards 92 that contain a plurality of spaced apart natural stones 94. The natural stones 94 are in one example tourmaline, which emit IR photos and also emit negative IR ions to aid in cleansing the air within the chamber 10. The grid 90 can be fixedly attached to the floor or slidably retained to the floor such that different grids 90 with different types of natural stones can be utilized.

The chamber 10 includes one or more salt blocks 98, such as Himalayan salt blocks to provide for halotherapy within the chamber 10. When heated, the salt blocks 98 emit ions that cleanse the air and when inhaled can also provide beneficial heath effects.

The chamber 10 also includes a plurality of arrays 100 of visible light emitting diodes. In the disclosed embodiment, the plurality of arrays 100 includes ten arrays located in the upper corners and the ceiling by the corners of the chamber 10. Each array 100 includes three hundred sixty lights 30 that emit red light having 640 nm wavelengths. The arrays 100 of red chromo-light modules provide for serene ambiance and illumination. While ten arrays are disclosed, any number of arrays with any number of lights emitting a selected wavelength is within the scope of the present disclosure.

The embodiments described herein relate to a full IR spectrum chamber wherein the FIR and/or NIR heaters or FIR and/or NIR emitters may be programmable to also emit MIR such that the same type of heater or emitter can be installed and configured or programmed to emit MIR. It is also contemplated that the FIR, NIR and MIR heaters or emitters can be distinct heaters or emitters configured only for FIR, NIR or MIR respectively. In one embodiment, for example, carbon fiber far infrared heaters (FIR) with low EMF emissions can be operably positioned in the chamber to surround the body with soothing infrared heat. Full spectrum infrared heaters, NIR or MIR/NIR heaters can provide near and mid-range infrared heating for immediate whole body heating. Ceramic mid far infrared heaters (MIR/FIR) heaters can be used to eliminate cold spots and provide addition mid and/or far infrared heat to the whole body.

Due to the efficiency of the IR heaters and the plurality of arrays 100, the chamber 10 can be powered utilizing a standard 120 V circuit with a 20-amp capacity. Further, the temperature and time of use can be controlled with a control panel 110 located within the chamber 10.

For example, the temperature in the chamber 10 is precisely controllable and the infrared sources warm the body with radiant heat. Thus, the chamber 10 is effective at lower temperatures than standard chambers, such that the chamber 10 can provide health benefits at lower temperatures such as those in the range of about 100° F. to about 150° F. The chamber 10 thus differs from typical dry heat chambers which require temperatures up to 180° F. to 200° F.

The control panel 102 may be a digital LED control panel and may further include one or more of speakers, AM/FM radio, Bluetooth capability, MP3/USB port(s), and speaker controls as well as chamber environment controls which allow for precise temperature and environment settings.

The chamber 10 may also include an oxygen ionizer as O2 ions can be introduced into the chamber 10 in order to cleanse, enhance and enrich the air within in the chamber 10. Additionally or alternatively, an ozone generator may be incorporated into the chamber 10 for introducing O3 to purify and deodorize the air.

In one embodiment, the chamber 10 may have exterior dimensions of about 47" wide, about 41" deep, and about 80" in height so that the chamber 10 comfortably fits two people. The dimensions can be increased accordingly to accommodate 3 or 4 people therein. The chamber may be constructed of a sustainable product or eco-friendly product such as aromatic Canadian Red cedar. Red cedar is toxin-free and natural wood having an aromatic quality.

The chamber 10 is shipped in a flat configuration to reduce shipping costs. The chamber 10 is sized to be assembled within any typically sized room including 8 feet by 10 feet by 9 feet in height. The walls 18, 20, 22, and 23 are assembled to the floor 14 and the ceiling 16 is secured to the walls 18, 20, 22, and 23. The door 24 is then attached to the front wall 23. As the heaters 54, 56 are efficient a typical 110 volt residential plug in can be utilized to supply power to the chamber 10. The modular nature of the chamber 10 allows the chamber 10 to be quickly assembled and disassembled such that if the chamber 10 is desired in a different room in a location or is to be moved, the chamber can be readily disassembled, moved to a new location and reassembled.

Although the present disclosure has been described with reference to preferred embodiments, workers skilled in the art will recognize that changes may be made in form and detail without departing from the spirit and scope of the disclosure.

The invention claimed is:

1. A chamber for providing controlled amounts of infrared radiation within an internal space sired to seat at least one human being, the chamber comprising:
   a front wall having, a door configured to move to provide ingress and egress to the chamber;
   a back wall;
   a left side wall connecting the front wall and the back wall; a right side wall connecting the front wall and the back wall;
   a floor abutting a bottom edge of each of the front wall, the back wall, the left side wall and the right side wall;
   a ceiling abutting a top edge of each of the front wall, the back wall, the left side wall and the right side wall;
   at least one heater attached to one of the front wall, the back wall, the left side wall or the right side wall, the at least one heater configured to emit far infrared radiation (FIR) energy, the at least one heater having a surface with an area; at least one light emitting source configured to emit a selected wavelength of visible light;
   at least one grid positioned over the area of the surface of one of the at least one heater configured to emit FIR energy and secured to one of the front wall, the back wall, the left side wall or the right side wall, and wherein the grid retains a plurality of natural stones substantially uniformly disposed on the grid and substantially uniformly positioned over the area of the surface of the at least one heater, wherein the plurality of natural stones emit infrared radiation (IR energy) when heated and wherein the grid comprises one or more spaces such that a portion of FIR photons from the at least one heater configured to emit FIR energy pass into the chamber at the same time a portion of the FIR photons are absorbed by the plurality of natural stones; and
   a control panel configured to control the duration of FIR and visible light within the chamber.

2. The chamber of claim 1 and further comprising a seat within the internal space.

3. The chamber of claim 1, the at least one heater comprising:
   a first heater of the at least three heaters is attached to the left side wall;
   a second heater of the at least three heaters is attached to the back wall;
   and a third heater of the at least three heaters is attached to the right side wall, wherein each of the first second and third heaters has a surface with an area and configured to emit FIR energy.

4. The chamber of claim 3, the at least one grid comprising:
   a first grid positioned over the area of the surface the first heater and attached to the left side wall;
   a second grid positioned over the area of the surface the second heater and attached to the back wall;
   and a third grid positioned over the area of the surface the third heater and attached to the right side wall;

wherein each of the first, second and third grids retains a plurality of natural stones substantially uniformly disposed on the grid and substantially uniformly positioned over the area of the surface of the first, second and third heaters, respectively, wherein the plurality of natural stones emit infrared radiation (IR energy) when heated and wherein each of the first, second and third grids comprises one or more spaces such that a portion of FIR photons from the first, second and third heaters pass into the chamber at the same time a portion of the FIR photons are absorbed by the plurality of natural stones.

5. The chamber of claim 1, wherein the at least one light emitting source configured to emit the selected wavelength of visible light comprises one or more arrays configured to emit red light at 640 nm.

6. The chamber of claim 1, wherein the at least one light emitting source configured to emit the selected wavelength of visible light comprises two or more arrays configured to emit red light at 640 nm.

7. The chamber of claim 1 and further comprising at least one heater configured to emit near infrared radiation (NIR) energy.

8. The chamber of claim 7, wherein the at least one heater configured to emit NIR energy comprises spaced apart heaters located on the left side wall and the right side wall.

9. The chamber of claim 7, wherein the control panel is configured to control the duration of FIR, NIR, and visible light within the chamber.

10. The chamber of claim 1, wherein the natural stones comprise jade, rosemary, quartz, germanium, Bian, tourmaline or combinations thereof.

11. The chamber of claim 1, wherein the at least one grid is removably retained in front of the at least one FIR heater.

12. The chamber of claim 1 further comprising a grid attached to a floor, wherein the grid includes a plurality of natural stones.

13. The chamber of claim 12, wherein the natural stones comprise jade.

14. The chamber of claim 1 and further comprising at least one salt block supported on an interior wall of the chamber.

15. The chamber of claim 1, further comprising at least one heater configured to emit MIR energy that is located within the chamber.

16. A chamber for providing controlled amounts of infrared radiation within an internal space sized for at least one human being, the chamber comprising:
    at least one emitter attached to a wall of the chamber, the at least one emitter configured to emit far infrared radiation (FIR) energy, the at least one emitter having a surface with an area;
    at least one light emitting source configured to emit a selected wavelength of visible light;
    at least one grid positioned over the surface of at least one emitter and secured to the wall of the chamber, the at least one grid supporting a plurality of natural stones substantially uniformly disposed on the grid and substantially uniformly positioned over the area of the surface of the at least one heater, wherein the plurality of natural stones emit infrared radiation (IR energy) when heated and wherein the grid comprises one or more spaces such that a portion of FIR photons from the at least one heater configured to emit FIR energy pass into the chamber at the same time a portion of the FIR photons are absorbed by the plurality of natural stones;
    and a control panel configured to control the amount and duration of FIR and visible light within the chamber such that the emitted FIR energy elevates the temperature within the chamber a temperature between about 100° F. and about 150° F.

17. The chamber of claim 16 further comprising at least one of an oxygen ionizer, a salt block, and a mineral block.

18. The chamber of claim 16 further comprising:
    at least one emitter configured to emit mid infrared radiation (MIR) energy;
    and at least one emitter configured to emit near infrared radiation (NIR) energy;
    and wherein each of the FIR, MIR, and NIR emitters are activated concurrently to provide near, mid-range, and far infrared heating concurrently.

* * * * *